United States Patent [19]

Mikkelsen

[11] Plant 4,190

[45] Jan. 17, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,002

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel Impatiens variety having variegated foliage, light pink flowers, and a compact plant habit.

1 Drawing Figure

1

The present invention relates to a new and distinctive cultivar of Impatiens plant, botanically known as Impatiens, and known by the cultivar name Betsy Ross. The new cultivar was developed by me through controlled breeding by crossing the unpatented cultivar Cheers (seed parent), a cultivar of the U.S. Department of Agriculture with unpatented cultivar number 74-92-13 (pollen parent), a seedling of James C. Mikkelsen. Asexual reproduction of terminal or stem cuttings has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. A short compact plant with very close internodes compared with the seed parent Cheers.
2. The foliage is thicker and larger than Cheers.
3. The flowers are a light pink that fade to nearly white under high light.
4. The overall texture of the foliage and general appearance of the plant more resembles a Croton than an Impatiens.
5. When placed indoors by a well lighted window, the new cultivar has been known to survive for upwards of 6 months, whereas the cultivar Cheers at best will only survive for several weeks.
6. Cutting production from vegetative shoots root in 8 to 10 days. Shoot production is 50% less than for the cultivar Cheers.
7. The highly variegated foliage is the center of attraction, with the flowers providing a pleasing accent. The central variegation increases in width under poor light conditions and varies in color from a light yellow to pale yellow or cream under low levels of light.

The accompanying colored photograph illustrates the overall appearance of this cultivar, and shows the colors as true as it is reasonably possible to obtain in a colored reproduction of this type.

The following is a detailed description of my new Impatiens cultivar based on plants produced under commercial practices at the greenhouses of Mikkelsens, Inc., at Ashtabula, Ohio. Color references are made to the Royal Horticultural Society Colour Chart except where general terms of ordinary dictionary significances are used.

2

Parentage: A controlled cross of the cultivar Cheers as the seed parent pollinated with Mikkelsen seedling number 74-92-13.

Propagation: By tip cuttings.

*Time to root.*—7–10 days at 20°–21° C summer, 14 days at 20° C winter.

*Rooting habit.*—Is typical for Impatiens; rapid, dendritic, fibrous and very abundant in primary and secondary roots.

Plant description:

*Form.*—A compact, short, vigorous, upright herb.

*Habit of growth.*—Slow, vigorous, upright, durable.

*Foliage description.*—Young cuttings during summer propagation are usually all green. As plant matures the terminal foliage becomes highly variegated, whorled with up to 14 leaves. Size: Leaves varies depending on the number of growing shoots in any given unit of space; from 4–5 cm. wide by 10–11 cm. long with petiole up to 5–7 mm long. Shape: From elliptical to obovate, tips tend to be revolute, apex acuminate, base acute. Texture: Highly glabrous, rugose. Margin: Entire, finely ciliolate. Color: Young foliage, top side between 147A and 137A; underside 147B. Mature foliage, top side green outer area 147A, light inner area from yellow-orange 21C, fading to 8B; under side green outer area 147B-C, light inner area from yellow orange 21D fading to 8C. Venation: Pinnately.

Flowering description:

*Flowering habits.*—Flowering is considered sparse, occurring progressively around the whorl of leaves, flowers deteriorate within 2–3 days after complete opening.

*Natural flowering season.*—Flowering is indeterminate and occurs throughout the year.

*Flower bud description.*—Flower buds are conical and covered with three sepals. A hollow nearly colorless spur emerges from the bottom sepal.

*Flowers borne.*—Single flowers borne on a near colorless pedical 4–5 cm. long.

*Quanity of flowers.*—Sparse with 6–8 per whorl of leaves but less than one per leaf.

*Petals.*—Top and two bottom petals nearly heart shaped, two side petals nearly circular with outer edge slightly emarginate. Shape: Side petals 50% smaller than other three. Color: Top side in winter when opening, red 52-D, fading to 36C-D; under side 55C-D. Number of petals: Five. Size: Petals 15mm × 20mm., flowers 3–4 cm. in diameter. Slightly curved colorless spur 4 cm. lg.

*Reproductive organs.*—Stamens: One in number. Anther shape: Hooded, color white. Pollen color: Cream white. Pistils: Stigma shape: Circular, flat, irregular surface, color green. Style color: Light green. Ovaries: One in number; 2–3 mm. long, before fertilized, color green.

I claim:

1. A new and distinct cultivar of Impatiens known by the cultivar name Betsy Ross and particularly characterized as to novelty by the combined characteristics of compact growth habit with close internodes; thick and large foliage which is variegated, having central portions which varies from light yellow to cream depending on light conditions; light pink flowers and by its long lasting characteristic.

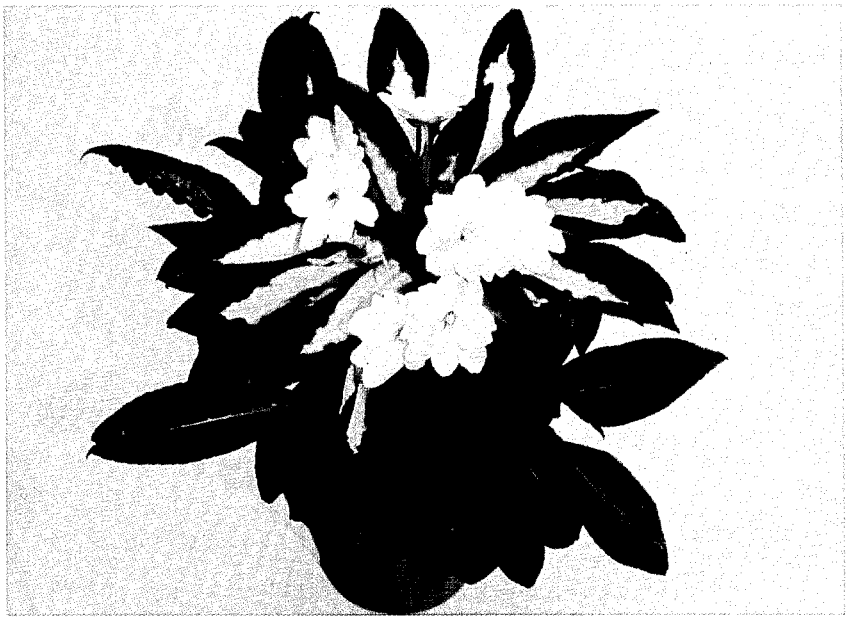

* * * * *